United States Patent [19]

O'Brien et al.

[11] Patent Number: 6,140,074
[45] Date of Patent: Oct. 31, 2000

[54] SH3 PROTEIN, GENE, CHIMERIC CELLS, VECTORS AND EXPRESSION METHOD FOR PRODUCING THE NOVEL PROTEIN, AND USES

[76] Inventors: Timothy J. O'Brien; Yinxiang Wang, both of 4301 W. Markham, Slot 718, Little Rock, Ark. 72205

[21] Appl. No.: 08/871,732

[22] Filed: Jun. 9, 1997

[51] Int. Cl.[7] .......................... C12P 21/02; C07H 21/04; C12N 15/63; C12N 9/12
[52] U.S. Cl. .................. 435/69.1; 435/194; 435/320.1; 536/23.1; 536/24.1
[58] Field of Search ................................ 435/320.1, 69.1, 435/194; 536/23.1, 24.1

*Primary Examiner*—Nancy Degen
*Attorney, Agent, or Firm*—Martin L. McGregor

[57] ABSTRACT

The invention is a protein having the amino acid sequence of Seq. I.D. No. 1 or an allelic variation retaining the biological activity of the protein having the amino acid sequence of Seq. I.D. No. 1, a DNA segment coding for a protein according to claim 1, preferably DNA segment according to claim 2 having the sequence of Seq. I.D. No. 2, or a substitution analog or allelic variation of Seq. I.D. No. 2, a chimeric cell comprising the DNA segment coding for a protein of Seq. I.D. No. 1, preferably a chimeric cell comprising the DNA segment of Seq. I.D. No. 2, a vector comprising a DNA segment coding for a protein having Seq. I.D. No. 1 operably linked to a promoter. The invention provides a preferred vector comprising the following components operably linked from 5' to 3': (a) a promoter; (b) a signal sequence; (c) 5' portion of a highly expressed gene endogenous to a selected host cell, (d) a linker sequence; all preceding the nucleotide sequence coding for TADG5 protein. The invention provides a protein production method which comprises expressing a DNA segment coding for a protein with the amino acid sequence of Seq. I.D. No. 1 in a chimeric host cell, preferably one which comprises expressing the DNA segment having the sequence of Seq. I.D. No. 2 or a substitution analog. The invention also provides peptides derived from TADG5 protein and further characterized by binding to an oligonucleotide having the sequence selected from the group consisting of Seq. I.D. Nos. 3, 4, 5, 6 7, 8, 9, 10, 11, 12, 13 or a strand complementary to one of the preceding sequences.

10 Claims, 15 Drawing Sheets

```
  1  gggccccta ctaaagcctt ggggttagta cgcgtgcgca gcagtttctt
                          ↑           ***
 51  ccgacagttg tgttgtgcca atggtggaga agaaaacttc ggttcgctcc
                          ---
101  caggacccccg ggcagcggcg ggtgctggac cgggctgccc ggcagcgtcg
151  catcaaccgg cagctggagg cccctgagaa tgacaacttc caggatgacc
201  cccacgcggg actccctcag ctcggcaaga gactgcctca gtttgatgac
251  gatgcggaca ctggaaaaga aagaagaaa acccgaggtg atcattttaa
301  acttcgcttc cgaaaaaact ttcaggcccct gttggaggag cagaacttga
351  gtgtggccga gggccctaac tacctgacgg cctgtgcggg accccccatcg
401  cggcccccagc gcccttctg tgctgtctgt ggcttcccat ccccctacac
451  ctgtgtcagc tgcggtgccc gtactgcac tgtgcgctgt ctggggaccc
501  accaggagac caggtgtctg aagtggactg tgtgagcctg ggcattccca
                                                  ***
551  gagaggaagg gccgctgtgc actgcccgc cttcagaaag acagaatttc
601  atcacccaat gcaggggag catttcctcg tccaagggag agcctcactc
651  ctgggaactg tctggcaggt aggctgggcc ccccagtgct gttagattaa
                                                  .....
701  aaatccctcgt gctggaaaaa aaaaaaaaaa aaaaa open reading frame (ORF) _____   initiation codon (Met) ---
inframe stop codon upstream of ORF ★★★
inframe stop codon downstream of ORF ***
polyadenylation signal .....          5' end of TADG5 →
```

FIG. 2

```
C-Fgr    alydy eArt--Edd  LtftkG ekfhiL nnte-G dwwearslssgkt
C-Tkl    alydy epth--dgd  LglkqG eklrvL ees--G ewwraQslttgqe
C-Abl    alydF vAsg--dnt  LSitkG eklrvL gynhnG ewceaQtk-ngq-
Ncf2a    vlfgF vpetkEE--  LqvmpG nivfvL kk---G ndnwatvmfngqk
Vav      aRydF cArdrsE--  LSlkEG diikiL nkk--G qqgwwrgeiygrv
Tadg5    fRknF qAll-EEqn  LSvaEG pn---yL taca-G ppsrpQrpfcavc
          *  *    *  *    *  *           *               *

C-Fgr    GciPSnY vapVds
C-Tkl    GliPhnf vamVns
C-Abl    GwvPSnY itpVns
Ncf2a    GlvPcmY lepVel
Vav      GwFPanY veedys
Tadg5    G-FPSpY tc-Vsc
          * **  *     *
```

FIG. 6A

```
Tadg5   RKNFQALLEEQNLSVAEGP..NYLTACAGPPSRPQRPFCAVCGFPSPYT
        | :| |       :||: ||.   .|.   :  :::::. :. |. ||. |.  -.
VAV     RYDFCA.RDRSELSLKEGDIIKILNKKGQQGWWRGEIYGRVGWFPANYV
```

FIG. 6B

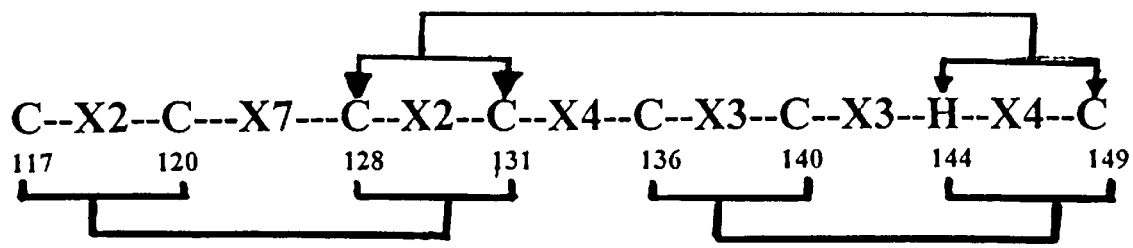

Putative zinc finger:

1. AA 124-151 of Tadg5 is homologous to zinc finger II of TF III:
    (identities: 35%,   positives: 57%)

```
              128  131              140   149
Tadg5   124-SPYTCVSCGARYCTVRCLGT HQE TR CLK-151
            +| |  |   | |    +        | +| +  |+|+|
TF III  104-NPYRCSQCGKAFRRTSDL S S HRRTQ C_I K-131
```

2. AA 111-133 of Tadg5 is homologous to zinc finger of a yeast protein:
    (identities: 47%,   positives: 56%)

```
              117   120           128 131
Tadg5   111-RPQRPFCAVCG FPSPYT CVSCGA-133
            | | |   +|    | | +      | | | | |
        370-RPQDSYCPHCGYYQYVECVSCHA-392
```

3. AA 121-149 of Tadg5 is homologous to zinc finger of a yeast protein:
    (identities: 48%,   positives: 65%)

```
                  136    140  144    149
Tagd5   121-GFP SPYTCVSCGA RYCTVRCLGTHQETRC-149
            | + |   +| |+| |   +  |+| . |     |  | | | |
        249-GYDSI S SCVNCGNK I CSVS CFKLHNETRC-277
```

FIG. 7

```
 19  cttcggttcgctcccaggacccccgggcagcggcctggtgctggaccgggct   68
     |||||||||||||||||||||||||||||||||||||||||||||||||||
 87  cttcggttcgctcccaggacccccgggcagcggcgggtgctggaccgggct  136

69  gcccggctgcgtcncatcaaccggcgcatcaaccggcagctggaggcccctggagaatgacta  118
     ||||||||||||| ||||||||||||||||||||||||||||||||||||  ||||||||||
137  gcccggcagcgtcgatcaaccggcgcatcaaccggcagctggaggcccctggagaatgacaa  186

119  ctttcaggatgactccca.tcgggactccctcnnctcggcaagagactgc  167
     ||||||||||||||||||  ||||||||||  ||||||||||||||||||
187  cttccaggatgaccccacgcgggactccctccctcagctcggcaagagactgc  236

168  ctcagtttgattactattcggacactggaaagaaanagaanaataacc  217
     |||||||||| ||||||||||||||||||||||  | :|  |||
237  ctcagtttgatgacgatgcggacactggaaagaaaagaagaaa...acc  283

218  cgaggtgatcatttaaacttcgcttccgaaaaactttcaggcccctgtt  267
     ||||||||||||||||||||||||||||||||||||||||||||||||
284  cgaggtgatcatttaaacttcgcttccgaaaaactttcaggcccctgtt  333
```

FIG. 9A-1

```
268  ggaggagcagaacttgagtgtggccgaggg.cctaactacctgacggcct  316
     |||||||||||||||||||||||||||||| |||||||||||||||||||
334  ggaggagcagaacttgagtgtggccgagggccctaactacctgacggcct  383

317  gtgcgggaccccccagcgcggccccttctgtctgtctgtggc  366
     |||||||||||||||||||||||||||||||||||||||||
384  gtgcgggaccccccagcgcggccccttctgtctgtctgtggc  433

367  ttccatcccctacacctgtgtcagctgtcagctgtactgcactgt  416
     ||||||||||||||||||||||||||||||||||||||||||||
434  ttccatcccctacacctgtgtcagctgtcagctgtactgcactgt  483

417  gcgctgtctgggaccaccaggagaccaggtgtctgaagtggactgtgt  466
     ||||||||||||||||||||||||||||||||||||||||||||||||
484  gcgctgtctgggaccaccaggagaccaggtgtctgaagtggactgtgt  533

467  gagcctgggcatt.ccagagaggaagggccgctgcactgcccggcctt  515
     ||||||||||||| |||||||||||||||||||||||||||||||||
534  gagcctgggcattcccagagaggaaggggccgctgcactgcccggcctt  583
```

FIG. 9A-2

```
516 cagaaagacagaattgcatcacccaatgcaggggggagctttcctggacn 565
        ||||||||||||||| ||||||||||||||| |||||||||| |||||
584 cagaaagacagaattcatcacccaatgcaggggggagcatttcctcgtcc 633

566 nagggaggngccgctcnttcaccaaacaaactgtgtctcatctgccagg 615
        : |||  ||
634 aagggag.......................................... 640

616 aaagaccagcttcactcctgggaacngtctggcaggtaggctgggcccc 665
                                    |||||||||||||||||||||
641 .........agcctcactcctggaactgtctggcaggtaggctgggcccc 683

666 cagtgctgttagaataaaaagcctcgtgccgg 697  HSU618
     ||||||||||||| ||||| |||| ||||| ||
684 cagtgctgttagattaaaaatcctcgtgctgg 715  TADG-5
```

FIG. 9A-3

```
  1  cggcncgagc  tcgtgccgct  tcggttcgct  cccaggaccc  cgggcagcgg
 51  ctggtgctgg  accgggctgc  ccgctgcgt   cncatcaacc  ggcagctgga
101  ggccctggag  aatgactact  ttcaggatga  ctcccatcgg  gactccctcn
151  nctcgcaag   agactgcctc  agtttgatta  ctattcggac  actggaaaga
201  aanagaanaa  naatacccga  ggtgatcatt  ttaaacttcg  cttccgaaaa
251  aactttcagg  ccctgttgga  ggagcagaac  ttgagtgtgg  ccgagggcct
301  aactacctga  cggcctgtgc  gggacccccca tcgcggcccc  agcgcccctt
351  ctgtgctgtc  tgtggcttcc  catcccccta  cacctgtgtc  agctgcggtg
401  cccggtactg  cactgtgtgc  tgtctggggga cccaccagga  gaccaggtgt
451  ctgaagtgga  ctgtgtgagc  ctgggcattc  cagagaggaa  gggccgctgt
501  gcactgcccg  gccttcagaa  agacagaatt  gcatcaccca  atgcaggggg
551  agcttttcct  ggacnnaggg  aggngccgct  cnttcaccaa  acaaaactgt
601  gtctcatctg  ccaggaaaga  ccagcttcac  tcctgggaac  ngtctggcag
651  gtaggctggg  cccccccagtg ctgttagaat  aaaaagcctc  gtgccgg
```

FIG. 9B

| CLONE | SEQUENCE | PROMOTER | OVERLAP/IDENTITIES |
|---|---|---|---|
| 12 | 5'CTGGCAATCTGANTA3' | | |
| 14 | 5'CTGGCAATCTGACTA3' | EBV | 12bp/ 100% |
| 18 | 5'TAGTCGGATGGTATG3' | | |
| 13 | 3'GGAGTTGGGGGGAGAA5' | PKA-R1α(hs) | 12bp/ 90% |
| 16 | 5'TAACTGGGGGTTAGAT3' | | |
| 15 | 5'TTTGTGGGTGGGGGG3' | HMG-14, ACTIN(hs) | 12bp/ 100% |
| 17 | 5'GGGTGGGGGGGTGGC3' | INSULIN (hs) | 14bp/ 92% |
| 22 | 5'TGGGGGGAGCGAATA3' | | |
| 23 | 5'TGAATCATGGGGGAC3' | | |
| 19 | 3'CAGCGAATTGGAAAG5' | | |
| 20 | 5'ATTGGTTAAGGCGAC3' | | |

FIG. 11

| Clone No. | Sequences | Group |
|---|---|---|
| 12 | 5'tagtcagattgccag3' | |
| 14 | 5'tagtcagattgccag3' | I |
| 18 | 5'tagtcggatggtatg3' | |
| consensus | tagtc-gat-g---g | |
| 13 | 3'ggagttgggggagaa5' | |
| 16 | 5'taactgggttagat3' | |
| 15 | 5'tttgtgggtgggggg3' | II |
| 17 | 5'gggtgggggggtggc3' | |
| 22 | 5'tggggggagcgaata3' | |
| 23 | 5'tgaatcatgggggac3' | |
| consensus | tgggggg | |
| 19 | 5'gaaaggttaagcgac3' | III |
| 20 | 5'attggttaaggcgac3' | |
| consensus | ggttaag | |

FIG. 12

SH3 PROTEIN, GENE, CHIMERIC CELLS, VECTORS AND EXPRESSION METHOD FOR PRODUCING THE NOVEL PROTEIN, AND USES

TECHNICAL FIELD

The present invention encompasses a novel protein designated TADG5 comprising a SH3 domain, a novel TADG5 DNA segment coding for the TADG5 protein, chimeric cells comprising the TADG5 DNA segment, vectors and plasmids comprising the TADG5 DNA segment and methods for producing the TADG5 protein as well as methods for using the TADG5 protein.

BACKGROUND OF THE INVENTION

Proteins containing SH3 domains have been previously identified. For example, chimeric protein tyrosine kinases comprising SH3 and SH2 domains are disclosed in U.S. Pat. No. 5,439,819. Proteins including SH2 and SH3 domains have been found to be important in cell cycle processes, especially in signal transduction pathways. Cyclin dependent kinases comprising SH3 domains are well known participants in signal transduction processes. SH2 domains interact specifically with various proteins containing phosphotyrosine residues, whereas SH3 regions bind guanine nucleotide releasing factors, believed to be involved in important signaling pathways. Numerous SH3 and SH2 domains in molecules involved in signal transduction are discussed by Koch et al., Science, 252:668–674 (1991).

Interfering in the intracellular signal transduction pathways may provide a mechanism for numerous therapeutic applications. While several proteins have been identified that interfere with various signal transduction mechanisms, new active proteins are important in providing alternatives for therapy and drug development. The novel protein of the invention provides a heretofore unknown molecule which binds to the promoter region of a number of important genes and the Epstein-Barr virus.

A partial DNA sequence recently entered into the database called HSU618 has 95% homology over approximately 560 nucleotides to the TADG5 gene, The HSU618 sequence does not in itself contain an open reading frame and indeed contains stop codons in all frames of the sequence as entered into the database. The sequence does however have a high homology with the TADG5 gene starting at nucleotide 87 of the TADG5 sequence and covering the TADG5 sequence through approximately base 654. This indicates the sequence as entered may be part of the TADG5 gene. HSU618 is indicated to have the capacity to bind cyclin G proteins. The HSU618 sequence was submitted by F. Xu from the University of Southern California. Because the HSU618 fragment lacks an open reading frame it cannot be expressed to produce the corresponding protein fragment, nor could it be said to suggest the TADG5 protein amino acid sequence nor to disclose the isolated and purified DNA segment coding for the TADG5 protein.

SUMMARY OF THE INTENTION

The invention is a novel TADG5 protein having the amino acid sequence set out in Seq. I.D. No. 1, novel TADG5 DNA segments coding for the TADG5 protein, including a DNA segment isolated from human genetic material set out in Seq. I.D. No, 2, or a construct comprising the open reading frame found beginning at base 71 (beginning the methionine codon) to base 532 or optionally through base 535 (end of the in frame stop codon downstream of the open reading frame). Preferably the open reading frame segment 71 to 532 or 535 is coupled with a promoter segment and optionally coupled with additional DNA coding for a fusion protein segment useful in purification such as a poly histidine tail or an enzyme such as GST. Such an embodiment of the subject invention may comprise one or more of the following components operably linked from 5' to 3' to form an expression plasmid vector: (a) a promoter, (b) a signal sequence; (c) 5' portion of a highly expressed endogenous gene preferably one whose product is secreted from the host cells (i.e. glucoamylase gene in Aspergillis); (d) a linker sequence; and (e) a nucleotide sequence corresponding to the desired TADG5 or TADG5 polypeptide fragment. Alternatively a resistance selectable marker gene may also be inserted after the TADG5 nucleotide sequence, following a transcription termination sequence, and having the appropriate components to function as a means for selecting clones containing the vector.

The invention also provides chimeric cells adapted to express the TADG5 protein, which preferably comprise vectors constructed as described above. The vectors may also include DNA coding for TADG5 fusion proteins. The invention further provides methods for production of the TADG5 protein including expression of the TADG5 DNA or substitution analogs thereof in chimeric cells.

In an alternate embodiment the invention provides a method of isolating and identifying promoter region DNA by treating a DNA sample with a cleavage agent to produce DNA segments, binding the DNA segments to the TADG5 protein or peptides derived from the TADG5 protein, isolating the DNA-protein or peptide complex, and releasing the DNA segment bound to the TADG5 protein. The invention further provides a method for effecting expression of genes by binding the TADG5 protein or peptides derived therefrom, or single stranded DNA homologous or complimentary to sequences found to bind to the TADG5 protein to the gene's promoter sequence in vivo, or in cell culture.

BRIEF DESCRIPTION OF THE DRAWINGS

The features and advantages of this invention will be evident from the following description when read in conjunction with the accompanying drawings:

FIG. 2 illustrates the sense nucleotide sequence of the TADG5 gene isolated from a cDNA ovarian library showing the open reading frame (ORF), initiation codon (Met), in frame stop codon in upstream of ORF, in frame stop codon in downstream of ORF, and polyadenylation signal (SEQ. ID NO: 2).

FIGS. 6A-6B show amino acid alignment of the SH3 domain of TADG5 with known SH3 domains showing the conserved amino acids between these domains.

FIG. 6B is a comparison of SH3-domains of TADG5 and VAV.

FIG. 7 is a comparison of TADG5's zinc finger domain to putative or known zinc finger domains of transcription factor 3 (TF3) and two yeast zinc finger domains showing the conserved nature of the appropriate cysteines and histidines.

FIGS. 9A-1, 9A-2, 9A-3 and 9B are show sequence comparison of TADG5 SEQ ID NO: 2 to the partial cDNA sequence of human putative cyclin G1 interacting protein (HSU618, SEQ ID NO: 16) showing 95% homology over approximately 560 nucleotides of the TADG5 gene.

FIG. 11 identifies clones isolated using the CASTing approach showing nucleotide sequence and percent identity to known promoter region sequences.

FIG. 12 lists subgroups of the isolated cloned nucleotide sequences.

DETAILED DESCRIPTION OF THE INVENTION

Figure 1A:
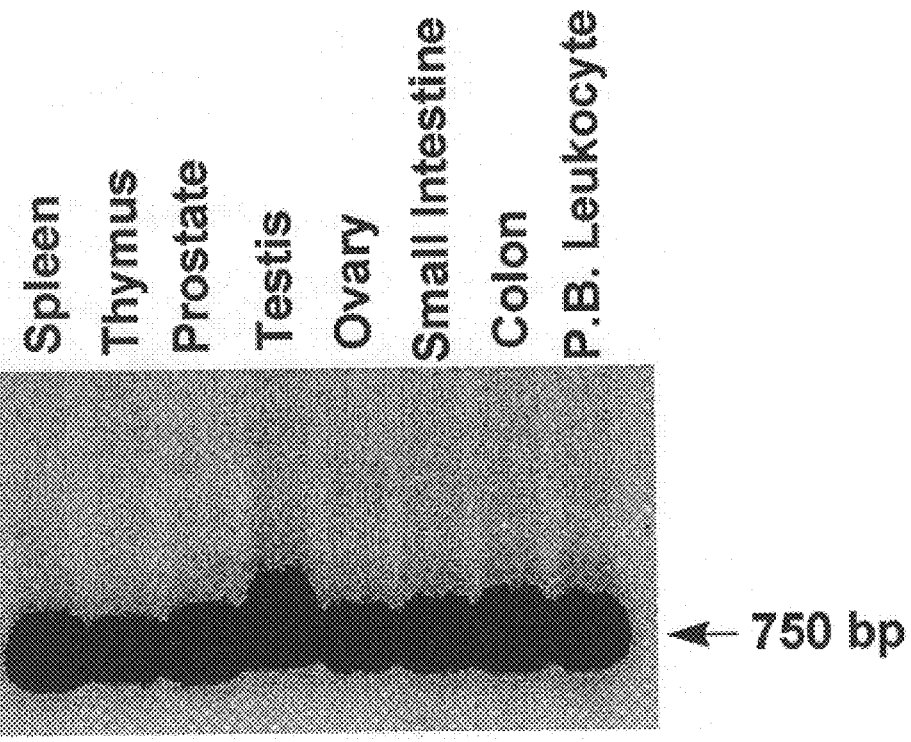
FIGS. 1A-1B are Northern blot analyses showing that the TADG5 gene is expressed in adult (FIG. 1A) and fetal (FIG. 1B) tissues to produce a corresponding mRNA.

The subject invention encompasses a novel protein TADG5 encoded by its novel amino acid sequence, a sense TADG5 DNA segment coding for the TADG5 protein, replacement analogs of the sense TADG5 DNA also coding for the TADG5 protein but having replacement of codons with other codons coding for the same amino acids, vectors and plasmids comprising a DNA segment coding for the TADG5 protein. Another embodiment of the subject invention comprises the following components operably linked from 5' to 3' to form an expression plasmid vector: (a) a promoter; (b) a signal sequence; (c) 5' portion of a highly expressed endogenous gene preferably one whose product is secreted from the host cells (i.e. glucoamylase gene in Aspergillis); (d) a linker sequence; and (e) a nucleotide sequence corresponding to the desired TADG5 protein or TADG5. Preferably the vector includes a resistance selectable marker gene. The invention also provides chimeric cells comprising a DNA segment coding for the TADG5 protein, and a method for producing the TADG5 protein as well as a method for using the TADG5 protein.

In an alternate embodiment the invention provides a method of isolating and identifying promoter region DNA by treating a DNA sample with a cleavage agent to produce DNA segments, binding the DNA segments to the TADG5 protein or peptides derived from the TADG5 protein, isolating the DNA-protein or peptide complex, and releasing the DNA segment bound to the TADG5 protein. The invention further provides a method for effecting expression of genes by binding the TADG5 protein or peptides derived therefrom, or single stranded DNA homologous or complimentary to sequences found to bind to the TADG5 protein to the gene's promoter sequence in vivo, or in cell culture.

The TADG5 protein comprises an SH3 domain, a zinc finger, a basic amino acid rich region, as well as a potential phosphorylation site. Nucleotide sequences which bind to the TADG5's zinc finger motif have been identified in several important genes including protein kinase A regulatory subunit gene ($R_{1\alpha}$), Epstein-Barr virus, gastrin, GADPH, beta-actin, HMG-14, Complement C5, and insulin. Of course the protein is useful as a source of amino acids, as a nutrition supplement, and as a marker for human tissue, as well as its primary role in cell cycle control. In addition, the protein itself or peptides generated from the protein sequence are useful as antigens for the production of polyclonal and monoclonal antibodies. Further, the gene itself is used as an antisense vehicle for cell cycle control by shutting down signaling or cell division. The cyclin proteins are known binders of cyclin-dependant kinase. As this process is part of the activation for the cell cycle control system and the cyclin complex also binds with tumor suppressor genes, cyclins have been found to be potent inhibitors of the cell cycle progression. The TADG5 gene is a binding partner for the cyclin-G proteins as demonstrated by the fact that the fragmentary sequence HSU618 was found to be associated with cyclin-G proteins, and has a high degree of homology with the TADG5 gene. The examples and description below further define the various embodiments of the invention.

Gene Isolation and Expression

Figure 1B:
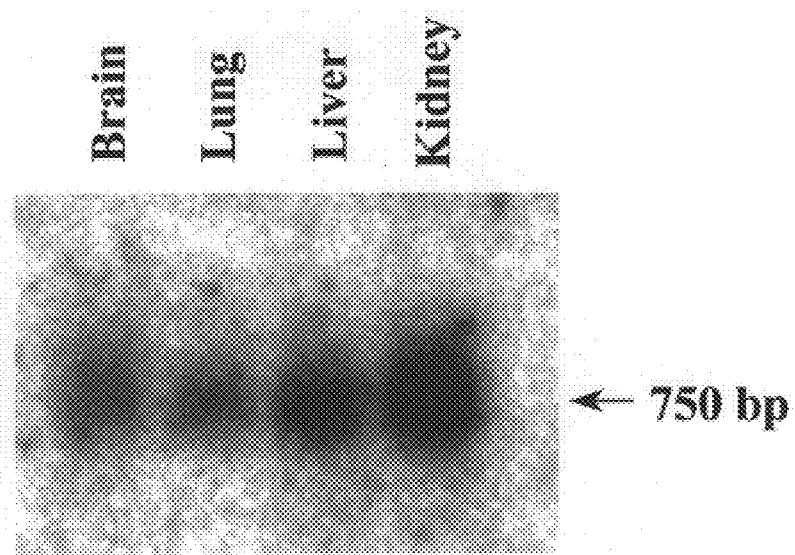

The novel gene, named TADG5, was identified and isolated as a PCR product perhaps differentially displayed between normal and ovarian carcinoma mRNA, and amplified using redundant primers for a SH3 domain. The PCR band selected, based on differential expression in tumor cDNA, was be subcloned as a 300 base pair amplified PCR product and sequenced. Specific primers synthesized to the 300 base pair sequence allowed gene amplification. The PCR product was used as a probe in Northern analysis to show that the novel TADG5 gene is expressed in adult and fetal tissues as an approximately 750 base pair mRNA (See FIG. 1). The TADG5 gene was shown to be expressed in adult tissues including; spleen, thymus, prostate, testes, ovary, small intestine, colon and leukocytes, as well as fetal tissues including; brain, lung, liver and kidney.

The PCR product produced by the above method was used subsequently as a probe to screen an ovarian cDNA library resulting in isolation of a positive clone containing 735 base pairs, including a poly-A tail (See FIG. 2). The isolated sense DNA sequence of this clone includes an open reading frame with a nucleotide stop codon upstream from the open reading frame, and a stop codon followed by a polyadenylation signal downstream from the open reading frame. Five prime race PCR, for example, using five prime anchored human lung cDNA further confirmed the five prime end of the novel gene and confirmed the sequence of the first 22 base pairs of the ovarian clone.

Figure 3:
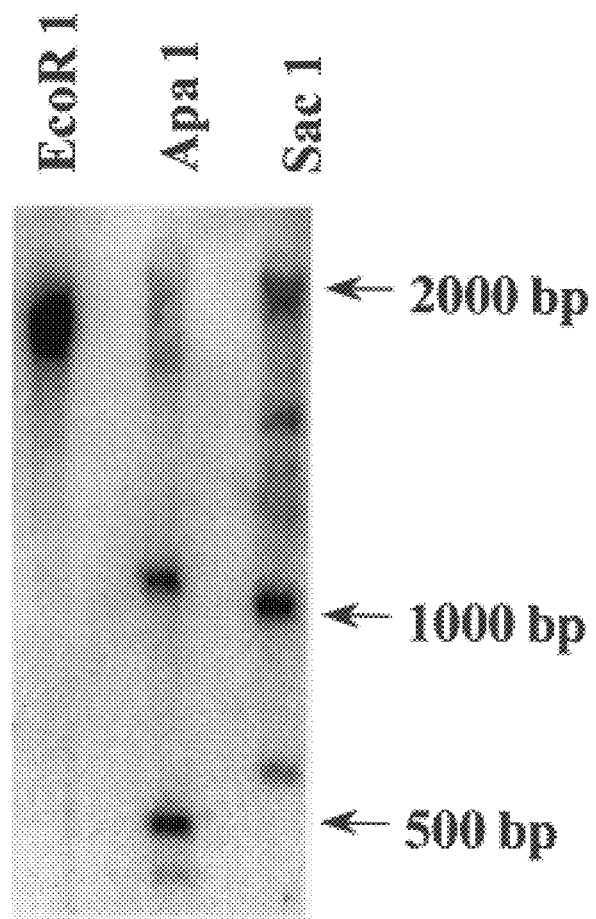
FIG. 3 is a Southern blot analysis of ovarian genomic DNA showing the presence of the TADG5 gene in the human genome.
Figure 4:
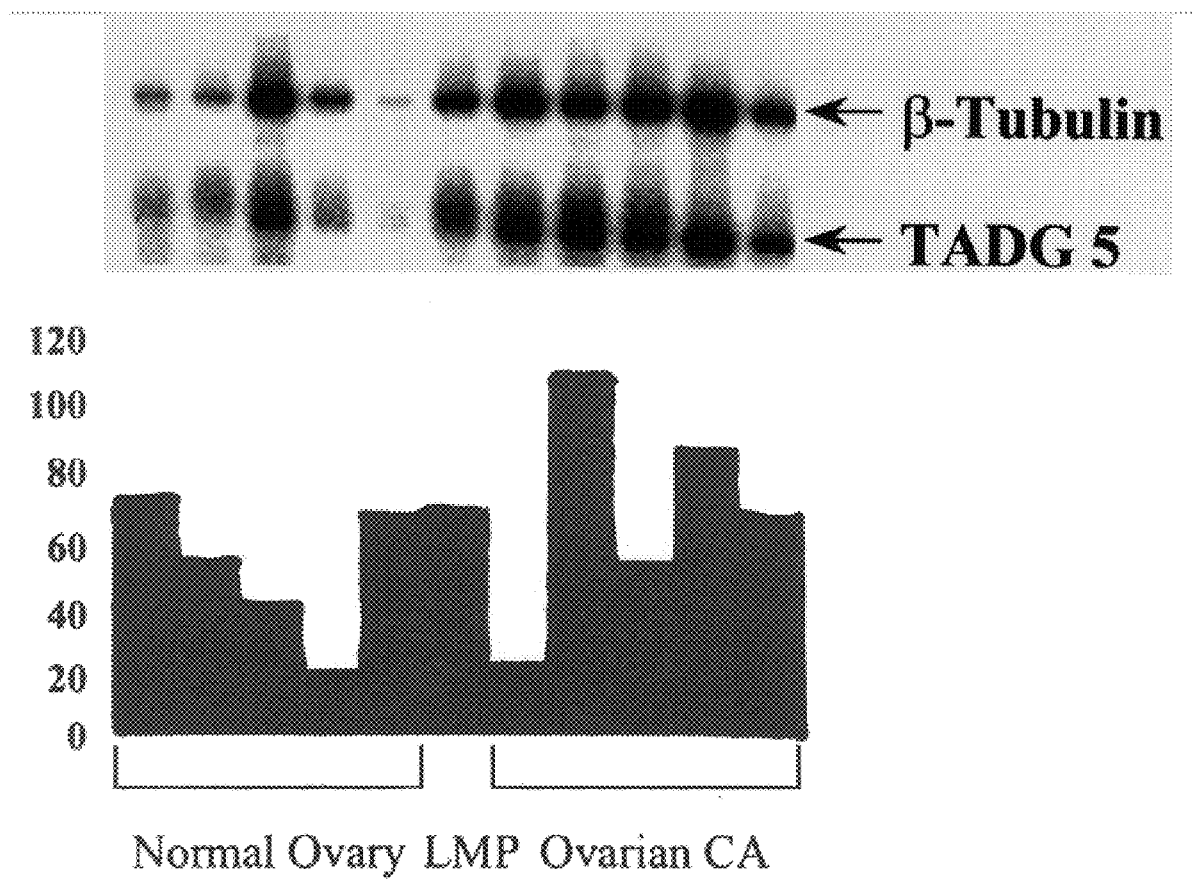
FIG. 4 is a quantitative PCR of the TADG5 gene showing that the TADG5 gene is expressed both in normal and tumor cDNA and that there may be some over expression in ovarian tumors relative to normal ovary.

The TADG5 gene was identified in ovarian genomic DNA. The ovarian cDNA clone produced above was used as a probe for Southern blot analysis to confirm the presence of the TADG5 gene in ovarian genomic DNA (See FIG. 3). The TADG5 gene contains known restriction sites for Apa I and Sac I restriction enzymes as determined from the ovarian cDNA clone sequence and as demonstrated by the presence of two or more bands as expected for these restriction enzyme digested lanes. Specific primers to internal sequences of the TADG5 gene are illustrated in table 1. The cDNA from both normal, low malignant potential tumors and ovarian carcinomas can be quantitatively amplified in the presence of an internal control gene (such as B-tubulin) to show that the TADG5 gene is expressed both in normal and tumor cDNA as shown in FIG. 4. These data suggest that TADG5 may be over expressed in high malignant potential tumors.

The TADG5 Protein

Figure 5:
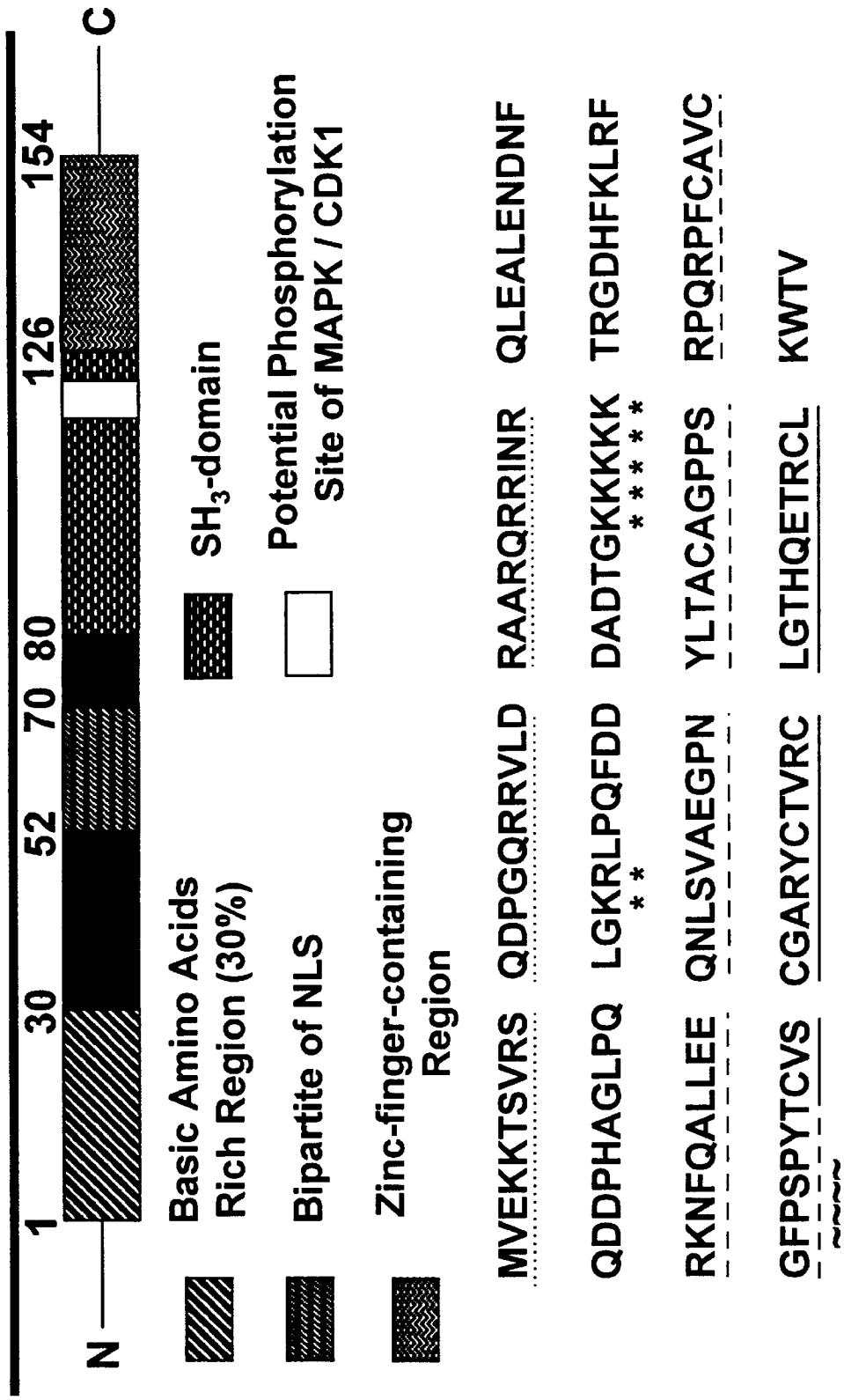
FIG. 5 is a diagram of the TADG5 protein showing the amino acid sequence and the various functional domains comprising of a SH3 domain, a zinc finger, a basic amino acid rich region, a bipartite nuclear localization sequence as well as a potential phosphorylation site (SEQ. ID NO: 1).

The invention provides a novel isolated and purified TADG5 DNA sequence coding for the TADG5 protein. The open reading frame of the TADG5 nucleotide sequence predicts a 154 amino acid protein with the initial codon for methionine at position 71 of the sequence. This continues through position 532 where a stop codon is identified. Examination of the 154 amino acid sequence demonstrates several functional domains as being conserved throughout the protein sequence as illustrated in FIG. 5. Beginning at the amino terminal end, the first 30 amino acids are recognized as a basic amino rich region. Downstream from this region at amino acid 52–70, a bipartite nuclear localizing sequence is recognized. Further downstream to at amino acid 80, a putative SH3 domain is recognized and extends approximately 50 amino acids. Downstream from the SH3 domain, a potential phosphorylation site for the map kinase enzyme is recognized. Finally, at the carboxyl terminal is a region recognized that contains putative zinc fingers.

These functional domains of the TADG5 protein indicate that this novel protein is a component of the signal transduction pathway system and that it interacts with other proteins through its SH3 domain. An alignment of amino acids in the SH3 domain confirms conserved amino acids in accordance with the general configuration of SH3 domains of known proteins (See FIG. 6). The bipartite nuclear localizing domain indicates that the TADG5 protein is localized in the nucleus and that the protein interacts with DNA either through the basic amino acid domain or through the zinc finger motif, or through both domains working in concert. A comparison of the zinc finger motif with known zinc fingers in both the TF3 (transcription factor 3) protein and in two yeast zinc finger proteins demonstrates the conserved nature of the appropriate cysteines and histidines to create such a zinc finger (See FIG. 7). Lastly, the TADG5 protein has the capacity to be activated and inactivated through phosphorylation by the map kinase signal system.

Production of TADG5 Protein and Expression Vectors

The invention provides a method of producing the TADG5 protein. For example, after synthesizing specific primers to allow amplification of the complete open reading frame sequence (See Table 1), the TADG5 DNA sequence can be integrated into a vector, and the TADG5 protein expressed in a chimeric cell using standard techniques as set out in "Molecular Cloning. A Laboratory Manual", 2d Edition, Cold Spring Harbor Laboratory Press (1989) Optionally the protein may be expressed as a fusion product such as with the carboxyl terminal region of the glutathione S-transferase ("GST") protein using a chimeric cell, such as an *E. coli* bacterial expression system.

The cDNA coding for the TADG5 protein is preferably inserted into an expression vector and expressed in a suitable host cell. The promoter useful in the present invention may be any that allows regulation of the transcription of the TADG5 cDNA. Preferably, the promoter is one such as Ptac or lac incorporated in the pGEX series of expression vectors available from Pharmacia of Uppsala Sweden. Pharmacia may also be contacted via the internet at http://www.biotech.pharmacia.se. Alternatively any of the many different promoters are known to those skilled in this art may be used but the inventors prefer to use the above listed promoters for expression in *E. coli* with the pGEX vector series. The signal sequence useful in the present method may be any that contains a translation initiation codon and secretory signal together with part of a coding region for any highly expressed endogenous gene, preferably those of the pGEX vector series.

The linker sequence useful in the present method contains a recognition sequence for any proteolytic enzyme, preferably a thrombin recognition sequence, as in the pGEX vector series.

The transcription termination sequence useful in the present method may be any that allows stabilization and correct termination of the TADG5 mRNA transcripts. Many different transcription termination sequences are known to those skilled in this art but the inventors prefer using those available for the pGEX vector series.

The selectable marker gene useful in the method of the present invention may be any that permits isolation of cells transformed with a TADG5 cDNA plasmid. Preferably, the selectable marker gene is selected from pyr4, pyrG, argB, trpC, amdS, or phleomycin or other antibiotic resistance genes.

Additionally, recombinant production of TADG5 protein is described below in its preferred embodiments. TADG5 can be produced in a number of host cells such as Aspergilits; *Saccharomyces cerevisiae, Kluyveromyces lactis*, or *Pichia pastorsis*; insect cells such as SF9; and mammalian cells such as Cos cells, Hela cells or the breast cancer tissue cell lines 231 and 435S as well as prokaryotic cells such as *E. coli*. The host cells, preferably *E. coli*. or mammalian cell lines, useful in the present invention are any that allow for integration of a vector, preferably a plasmid comprising the TADG5 cDNA and expression of the TADG5 cDNA.

The isolated DNA of Seq. I.D. No. 1 was inserted into an expression vector, pGEX, comprising a promoter, an initiation sequence, a DNA segment coding for GST, and a linker. The vector was inserted into *E. coli* and expressed.

Figure 8A:
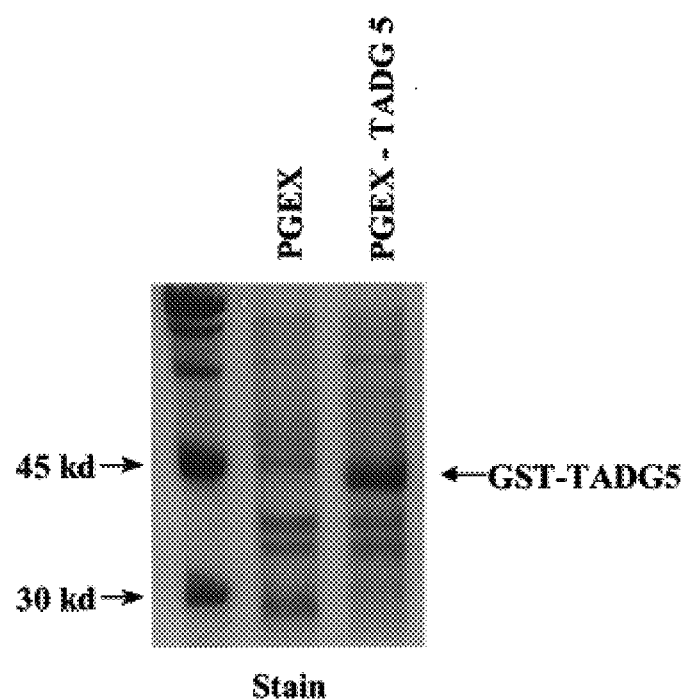
FIG. 8a is a polyacrylarnide gel electrophoresis analysis of GST-TADG5 fusion proteins expressed in E. coli and stained with coomaisse blue showing the molecular weight of the GST-TADG5 fusion protein to be 45 kd.

Molecular weight determination was performed by using polyacrylamide gel electrophoresis which confirmed expression of an anticipated 30 kd protein for the GST gene alone and a predicted 45 kd fusion product for the GST-TADG5 (See FIG. 8a).

Figure 8B:
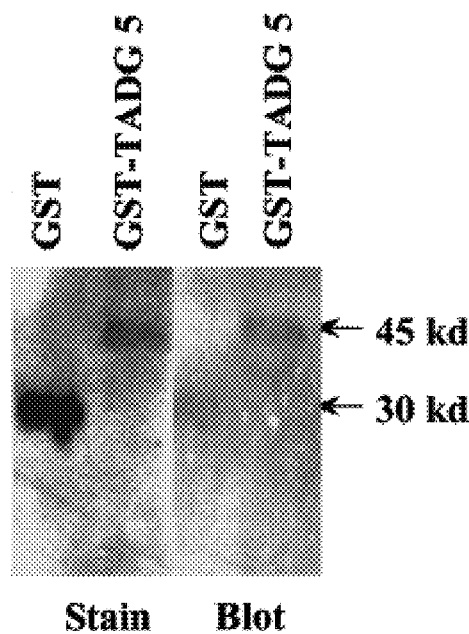
FIG. 8b is a Western analysis of GST-TADG5 fusion proteins expressed in E. coli confirming the expression of TADG5 in this bacterial expression system.

The invention further provides generation of antibodies against peptides of the novel protein. For example, peptides synthesized from the amino and carboxy terminal ends of the TADG5 amino acid sequence were used to raise polyclonal antibodies which in turn were used to confirm expression of TADG5 as a GST fusion protein in *E. coli*. Western analysis of the fusion protein confirmed the expression of this protein in this particular expression system (See FIG. 8b). Other polyclonal antibodies developed against peptides to the various functional domains also allow the identification of interacting proteins and nucleotide sequences with the TADG5 protein. Interruption of such interactions through the SH3 domain, map kinase phosphorylation motif, basic amino acid domain and zinc finger motif may be useful in restoring control of the cell cycle in certain tumor types.

As noted above a partial sequence recently entered into the database called HSU618 has about 95% homology over approximately 560 nucleotides to the TADG5 gene. The HSU618 sequence (SEQ ID NO: 16) does not in itself contain an open reading frame and indeed contains many stop codons in all frames of the sequence as entered into the database. Therefore the sequence neither discloses the novel protein nor can the sequence per se be cloned and expressed to yield the novel protein. The sequence does however have a high homology with the TADG5 gene starting at nucleotide 87 of the TADG5 sequence and covering the TADG5 sequence through approximately base 654, as shown in FIG.

9. This indicates the sequence as entered may be part of the TADG5 gene with some sequencing errors or differences, and that TADG5 may have the capacity to bind cyclin G proteins as this sequence was identified based on its capacity to associate with cyclin G proteins. The cyclins are known binders of cyclin-dependent kinase. Cyclin binding with cyclin dependent kinase is part of the activation for the cell cycle control system. The cyclin/cyclin dependent kinase complex also binds with tumor suppressor genes, as such they are inhibitors of the cell cycle progression. TADG5 may act as a binding partner for the cyclin-G proteins. A comparison of the sequence differences between HSU618 and TADG5 gene is shown in FIG. 9. Especially important is the lack of the initiation sequence at bases 71–73, which means that HSU618 cannot be expressed.

The invention further provides a method of using the novel protein produced and isolated by the above method. The isolated protein is hydrolyzed, for example, with pepsin, trypsin, chymotrypsin, elastase, carboxypeptidase, aminopeptidase and dipeptidase to produce smaller peptide fragments and individual amino acids, in order to provide essential and nonessential amino acids of nutritional importance (Harper, A. E. Amino acids of nutritional importance. In Toxicants occurring naturally in foods, ed. Committee on Food Protection, Food and Nutritional Board, National Research Council, 2nd ed. Washington, D.C.: National Research Council, 1973).

EXAMPLE 1

Identification of Binding Sequences

The invention further provides an additional method for using the TADG5 protein. Expression of the GST-TADG5 fusion product in a bacterial expression system as described above, for example, allows direct evaluation of the DNA-binding capacity of the TADG5 protein, either through the basic amino acid region domain or the zinc finger motif. *E. coli* was used to express the fusion product, and the expressed, secreted fusion protein was subsequently isolated from other proteins by binding of the GST moiety to glutathione conjugated sepharose beads as follows: The host cells were ruptured by sonication. The fusion protein was bound to Glutathione Sepharose 4B equilibrated with 1×PBS using 2 ml of 50% slurry to each 100 ml of sonicate in 1×PBS including 1% Triton X-100 and 1 mM PMSF. The resulting mixture was incubated 15 mins with gentle agitation then at 4° C. overnight. The suspension was then centrifuged at 500 g for 5 minutes to sediment the matrix. The supernate was removed and the pellet washed with 10 bed volumes of 1×PBS. (Bed volume is equal to 0.5×volume of 50% Glutathione Sepharose slurry used). The suspension was centrifuged at 500 g for 5 minutes to sediment the matrix, and the wash discarded, the wash was repeated three times. The fusion protein was eluted by addition of a buffer 10 mM glutathione and 50 mM Tris-HCL (pH 8.0) equal to the bed volume of the washed, sedimented matrix. The sediment/buffer was mixed gently to resuspend the matrix. The resulting suspension was incubated at room temperature (22–25° C.) for 10 minutes to elute the fusion protein from the matrix.

Figure 10:
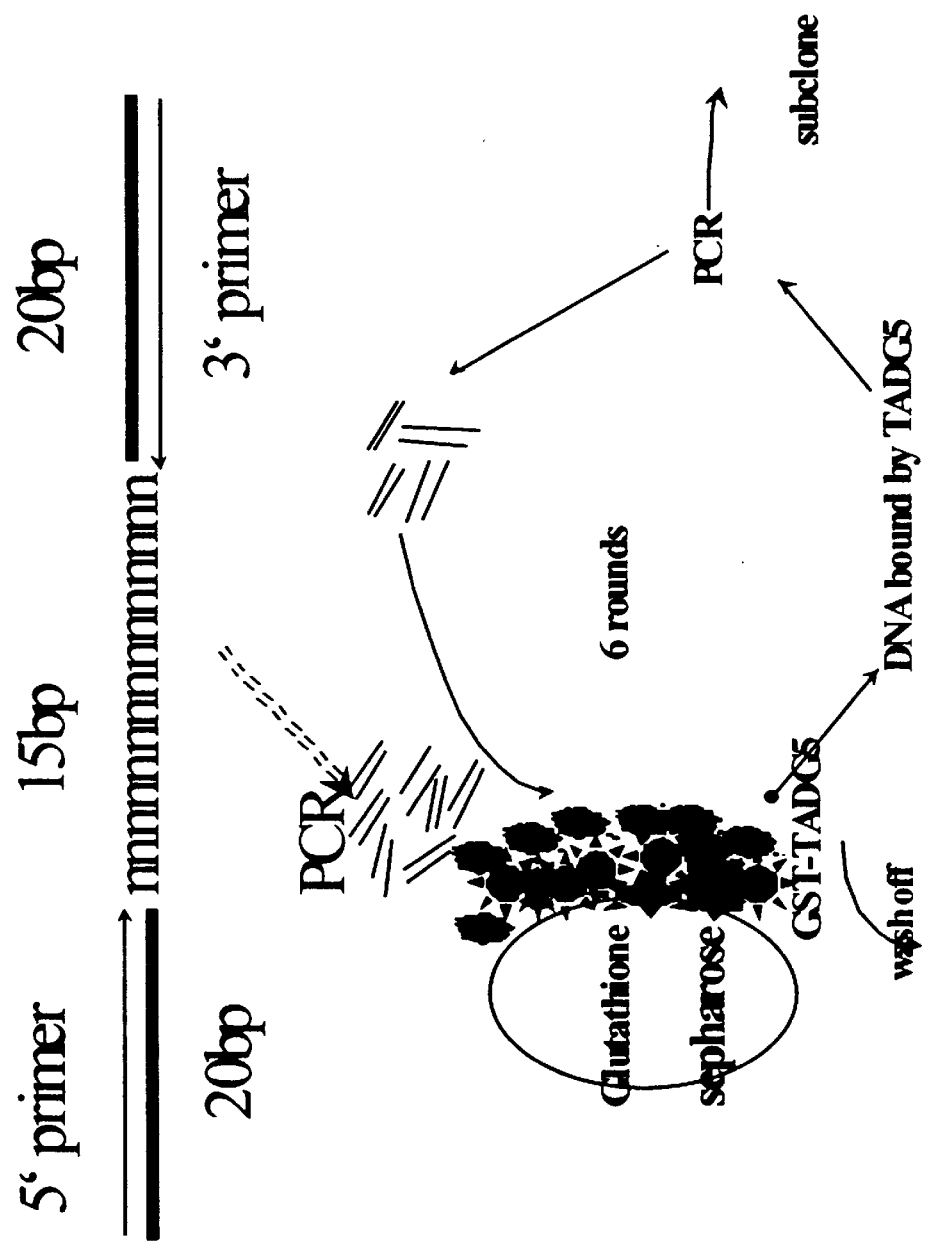
FIG. 10 illustrates the CASTing approach used to isolate nucleotide sequences that may bind to TADG5's basic amino acid rich region or zinc finger motif.

As shown in FIG. 10, nucleotide sequences that bind to either the basic amino acid region and/or the zinc finger motif of the TADG5 protein were isolated using the GST-TADG5 fusion protein. The sepharose:protein:DNA complexes were collected by centrifugation and washed. The DNA was purified from the complex, cloned and sequenced. Eleven clones sequenced are shown in FIG. 11. They all have a core (consensus) identical sequence as underlined and may be further subgrouped into three categories as indicated in FIG. 12. The clones were found to be DNA segments from the promoter regions of the several genes as well as the Epstein Barr Virus. The clones are useful as probes for identifying and amplifying the corresponding promoter regions or as binding agents to interfere with expression of the corresponding genes.

Definitions

The term "substitution analog" or "allelic variation" or "allelic variant" all refer to a DNA sequence which one or more codons specifying one or more amino acids of TADG5 or a TADG5 polypeptide are replaced by alternate codons that specify the same amino acid sequence with a different DNA sequence. Where "substitution analog" or "allelic variant" refers to a protein or polypeptide it means the substitution of a small number, generally five or less amino acids as are known to occur in allelic variation in human and other mammalian proteins wherein the biological activity of the protein is maintained.

The term "vector(s)" means plasmid, cosmid, phage or any other vehicle to allow insertion, propagation and expression of TADG5 cDNA.

The term "host(s)" means any cell that will allow TADG5 expression.

The term "promoter(s)" means regulatory DNA sequences that control transcription of the TADG5 cDNA.

The term "transformation" means incorporation permitting expression of heterologous DNA sequences by a cell.

The term "polypeptide" or "polypeptides" means several amino acids attached together to form a small peptide or polypeptide.

"Chimeric cell" means a cell whose DNA has been altered compared to a normal cell of the same organism.

"DNA coding for a protein" means DNA sequences which produce a particular primary amino acid sequence.

EXAMPLE 2

Preparation of Substitution Analogs

Due to the redundancy of the DNA code there are millions of DNA sequences that would produce a particular amino acid sequence when expressed. Given the amino acid sequence, for example Seq. I.D. No. 1, one can substitute into the natural DNA sequence, such as Seq. I.D. No. 2, alternative codons for the desired amino acids to produce an alternative DNA sequence also coding for the novel protein. One may find that particular chimeric cells of a particular expression method favor particular mRNA codons for a particular amino acid. Altering the human DNA sequence to increase the frequency of favored codons may improve the expression efficacy in a chimeric cell, thus improving the efficacy of the expression process. The sequences may be derived by substitution of redundant codons for the amino acid sequences and splicing the substituted sequences into the natural gene by routine methods well known in the art. It is impractical to attempt to list all the millions of DNA sequences that may code for the claimed sequence. However, the invention comprises the novel protein, its novel amino acid sequence, and all DNA sequences natural or synthetic coding for the novel amino acid sequence. These substitution analogs may be constructed in the following manner: Table 1 lists the alternative codons that code for the 20 common amino acids. DNA sequence substitution analogs that also code for human TADG5 can be constructed by choosing alternate codons from Table 1 to alter the DNA Sequence between a pair of restriction enzyme cleavage sites, as are well known in the art. Alternative codons are assembled into a synthetic oligonucleotide by conventional methods and the synthetic oligo is substituted into the endonuclease treated DNA of Sequence ID. No. 2 by the methods described in "Molecular Cloning. A Laboratory Manual", 2d Edition, Cold Spring Harbor Laboratory Press (1989), to produce a substitution analog. Other methods generally known to those skilled in the art can also be employed to obtain substitution analogs of DNA sequences. The alteration of the DNA by cleavage and codon substitution maybe repeated to substitute substantial portions of the original DNA sequence with alternative codons without altering the protein amino acid sequence of Sequence ID. No. 1. Alteration of a DNA sequence which produces no change in the protein expressed by the DNA sequence might, for example, be conducted to increase protein expression in a particular host cell by increasing the occurrence of codons that correspond to amino acid tRNAs found in higher concentration in the host cell. Such altered DNA sequences for substitution analogs can be easily produced by those of ordinary skill in the art following the method set out above, or other alternative techniques for altering the DNA sequence while obtaining the same protein on expression. Substitution analogs can be obtained by substitution of oligonucleotides at restriction cleavage sites as described above, or by other equivalent methods that change the codons while preserving the amino acid sequence of the expressed protein.

TABLE 1

| Amino Acid | One Letter Symbol | 3 Letter Symbol | DNA CODON |
|---|---|---|---|
| Alanine | A | ala | GCT, GCC, GCA, GCG |
| Arginine | R | arg | CGT, CGC, CGA, CGG, AGA, AGG |
| Asparagine | N | asn | AAT, AAC |
| Aspartic Acid | D | asp | GAT, GAC |
| Cysteine | C | cys | TGT, TGC |
| Glutamic Acid | E | glu | GAA, GAG |
| Glutamine | Q | gln | CAA, CAG |
| Glycine | G | gly | GGT, GGC, GGA, GGG |
| Histidine | H | his | CAT, CAC |
| Isoleucine | I | ile | ATT, ATC, ATA |
| Leucine | L | lue | TTA, TTG, CTT, CTC, CTA, CTG |
| Lysine | K | lys | AAA, AAG |
| Methionine | M | met | ATG |
| Phenylalanine | F | phe | TTT, TTC |
| Proline | P | pro | CCT, CCC, CCA, CCG |
| Serine | S | ser | TCT, TCC, TCA, TCG, AGT, AGC |
| Threonine | T | thr | ACT, ACC, ACA, ACG |
| Ttyptophan | W | trp | TTG |
| Tyrosine | Y | tyr | TAT, TAC |
| Valine | V | val | GTT, GTC, GTG, GTG |

Those skilled in the art will recognize many variations are possible in substituting conserved amino acids in the protein sequence which will produce variations in sequence without seriously changing the biological activity of the protein. In addition certain peptides may be made by selective enzymatic cleavage of the TADG5 protein or by synthesis of selected peptide sequences. These peptides will retain the binding characteristics of the intact protein and may be substituted for the protein in certain applications. Peptides may also be used to raise antibodies against the intact protein. Sequence ID Nos. 14 and 15 illustrate two peptides that have produced polyclonal antibodies which bind the TADG5 protein. Those skilled in the art will recognize that many variations may be made within the scope of the claims set out below which define the invention described herein.

We claim:

1. An isolated DNA segment coding for a TADG5 protein having the amino acid sequence of Seq. I.D. No. 1 or an allelic variation thereof which retains the biological activity of the TADG5 protein.

2. The DNA segment according to claim 1 having the sequence of Seq. I.D. No. 2, or a substitution analog or allelic variation of Seq. I.D. No. 2 which encodes a protein having TAGD5 biological activity.

3. A chimeric host cell comprising the DNA segment of claim 2.

4. A vector comprising a DNA segment according to claim 1 operably linked to a promoter.

5. A chimeric host cell comprising the vector of claim 4.

6. The vector according to claim 4 further comprising the following components operably linked from 5' to 3': (a) a promoter; (b) a signal sequence; (c) 5' portion of a highly expressed gene endogenous to a selected host cell; (d) a linker sequence; all preceding the DNA segment coding for a TADG5 protein.

7. A chimeric host cell comprising the vector of claim 6.

8. A chimeric host cell comprising the DNA segment of claim 1.

9. A protein production method which comprises expressing a DNA segment coding for a protein having the amino acid sequence of Seq. I.D. No. 1 or an allelic variation thereof which retains the biological activity of the TADG5 protein in a chimeric host cell.

10. The protein production method according to claim 9 which comprises expressing the DNA segment having the sequence of Seq. I.D. No. 2 or a substitution analog thereof which encodes a protein having TAGD5 biological activity in a chimeric host cell.

* * * * *

UNITED STATES PATENT AND TRADEMARK OFFICE
CERTIFICATE OF CORRECTION

PATENT NO. : 6,140,074
DATED : October 31, 2000
INVENTOR(S) : Timothy O'Brien, et al.

It is certified that error appears in the above-identified patent and that said Letters Patent is hereby corrected as shown below:

On the cover page, please list the Board of Trustees of the University of Arkansas System as the Assignee. An Assignment was recorded on REEL/FRAME 8687/0700 on 6/9/97.

Signed and Sealed this

Twenty-second Day of May, 2001

Attest:

NICHOLAS P. GODICI

Attesting Officer

Acting Director of the United States Patent and Trademark Office

SEQUENCE LISTING (1) GENERAL INFORMATION:

(iii) NUMBER OF SEQUENCES: 16

(2) INFORMATION FOR SEQ ID NO: 1:

(i) SEQUENCE CHARACTERISTICS:
      (A) LENGTH:     154 AMINO ACIDS
      (B) TYPE:       AMINO ACID
      (C) STRANDEDNESS: SINGLE
      (D) TOPOLOGY:   LINEAR (ii) MOLECULE TYPE:   PROTEIN (xi) SEQUENCE DESCRIPTION: SEQ ID NO: 1:

Met Val Glu Lys Lys Thr Ser Val Arg Ser Gln Asp Pro Gly Gln
             5                    10                   15

Arg Arg Val Leu Asp Arg Ala Ala Arg Gln Arg Arg Ile Asn Arg
            20                   25                  30

Gln Leu Glu Ala Leu Glu Asn Asp Asn Phe Gln Asp Asp Pro His
            35                   40                  45

```
Ala Gly Leu Pro Gln Leu Gly Lys Arg Leu Pro Gln Phe Asp Asp
            50                      55                      60

Asp Ala Asp Thr Gly Lys Lys Lys Lys Thr Arg Gly Asp His
            65                      70                      75

Phe Lys Leu Arg Phe Arg Lys Asn Phe Gln Ala Leu Leu Glu Glu
            80                      85                      90

Gln Asn Leu Ser Val Ala Glu Gly Pro Asn Tyr Leu Thr Ala Cys
            95                     100                     105

Ala Gly Pro Pro Ser Arg Pro Gln Arg Pro Phe Cys Ala Val Cys
           110                     115                     120

Gly Phe Pro Ser Pro Tyr Thr Cys Val Ser Cys Gly Ala Arg Tyr
           125                     130                     135

Cys Thr Val Arg Cys Leu Gly Thr His Gln Glu Thr Arg Cys Leu
           140                     145                     150

Lys Trp Thr Val
```

(2) INFORMATION FOR SEQ ID NO: 2:

(i) SEQUENCE CHARACTERISTICS:
        (A) LENGTH: 735 BASE PAIRS
        (B) TYPE: NUCLEIC ACID
        (C) STRANDEDNESS: SINGLE
        (D) TOPOLOGY: LINEAR (ii) MOLECULE TYPE: OTHER NUCLEIC ACID (iii) HYPOTHETICAL: NO (iv) ANTI-SENSE: NO (xi) SEQUENCE DESCRIPTION: SEQ ID NO: 2:

```
GGGGCCCCTA CTAAAGCCTT GGGGTTAGTA CGCGTGCGCA GCAGTTTCTT        50
CCGACAGTTG TGTTGTGCCA ATGGTGGAGA AGAAAACTTC GGTTCGCTCC       100
CAGGACCCCG GGCAGCGGCG GGTGCTGGAC CGGGCTGCCC GGCAGCGTCG       150
CATCAACCGG CAGCTGGAGG CCCTGGAGAA TGACAACTTC CAGGATGACC       200
CCCACGCGGG ACTCCCTCAG CTCGGCAAGA GACTGCCTCA GTTTGATGAC       250
GATGCGGACA CTGGAAAGAA AAAGAAGAAA ACCCGAGGTG ATCATTTTAA       300
ACTTCGCTTC CGAAAAAACT TTCAGGCCCT GTTGGAGGAG CAGAACTTGA       350
GTGTGGCCGA GGGCCCTAAC TACCTGACGG CCTGTGCGGG ACCCCCATCG       400
CGGCCCCAGC GCCCCTTCTG TGCTGTCTGT GGCTTCCCAT CCCCCTACAC       450
CTGTGTCAGC TGCGGTGCCC GGTACTGCAC TGTGCGCTGT CTGGGGACCC       500
ACCAGGAGAC CAGGTGTCTG AAGTGGACTG TGTGAGCCTG GCATTCCCA        550
GAGAGGAAGG GCCGCTGTGC ACTGCCCGGC CTTCAGAAAG ACAGAATTTC       600
ATCACCCAAT GCAGGGGGAG CATTTCCTCG TCCAAGGGAG AGCCTCACTC       650
CTGGGAACTG TCTGGCAGGT AGGCTGGGCC CCCCAGTGCT GTTAGATTAA       700
AAATCCTCGT GCTGGAAAAA AAAAAAAAAA AAAAA                       735
```

(2) INFORMATION FOR SEQ ID NO: 3:

(i) SEQUENCE CHARACTERISTICS:
        (A) LENGTH: 15 BASES
        (B) TYPE: NUCLEIC ACID
        (C) STRANDEDNESS: SINGLE
        (D) TOPOLOGY: LINEAR (ii) MOLECULE TYPE:  OTHER NUCLEIC ACID (iii) HYPOTHETICAL:  NO (iv) ANTI-SENSE:  NO (xi) SEQUENCE DESCRIPTION: SEQ ID NO: 3:

CTGGCAATCT GACTA                                                         15

(2) INFORMATION FOR SEQ ID NO: 4:

(i) SEQUENCE CHARACTERISTICS:
            (A) LENGTH: 15 BASE PAIRS
            (B) TYPE:  NUCLEIC ACID
            (C) STRANDEDNESS:  SINGLE
            (D) TOPOLOGY:  LINEAR (ii) MOLECULE TYPE:  OTHER NUCLEIC ACID (iii) HYPOTHETICAL:  NO (iv) ANTI-SENSE:  YES (xi) SEQUENCE DESCRIPTION: SEQ ID NO: 4:

CTGGCAATCT GACTA                                                         15

(2) INFORMATION FOR SEQ ID NO: 5:

(i) SEQUENCE CHARACTERISTICS:
            (A) LENGTH: 15 BASE PAIRS
            (B) TYPE:  NUCLEIC ACID
            (C) STRANDEDNESS:  SINGLE
            (D) TOPOLOGY:  LINEAR (ii) MOLECULE TYPE:  OTHER NUCLEIC ACID (iii) HYPOTHETICAL:  NO (iv) ANTI-SENSE:  NO (xi) SEQUENCE DESCRIPTION: SEQ ID NO: 5:

TAGTCGGATG GTATG                                                         15

(2) INFORMATION FOR SEQ ID NO: 6:

(i) SEQUENCE CHARACTERISTICS:
            (A) LENGTH: 15 BASE PAIRS
            (B) TYPE:  NUCLEIC ACID
            (C) STRANDEDNESS:  SINGLE
            (D) TOPOLOGY:  LINEAR (ii) MOLECULE TYPE:  OTHER NUCLEIC ACID (iii) HYPOTHETICAL:  NO (iv) ANTI-SENSE:  YES (xi) SEQUENCE DESCRIPTION: SEQ ID NO: 6:

AAGAGGGGGT TGAGG                                                         15

(2) INFORMATION FOR SEQ ID NO: 7:

(i) SEQUENCE CHARACTERISTICS:
            (A) LENGTH: 15 BASE PAIRS
            (B) TYPE:  NUCLEIC ACID
            (C) STRANDEDNESS:  SINGLE
            (D) TOPOLOGY:  LINEAR (ii) MOLECULE TYPE:  OTHER NUCLEIC ACID (iii) HYPOTHETICAL:  NO (iv) ANTI-SENSE: NO (xi) SEQUENCE DESCRIPTION: SEQ ID NO: 7:

TAACTGGGGT TAGAT                                                    15

(2) INFORMATION FOR SEQ ID NO: 8:

(i) SEQUENCE CHARACTERISTICS:
            (A) LENGTH: 15 BASE PAIRS
            (B) TYPE:  NUCLEIC ACID
            (C) STRANDEDNESS: SINGLE
            (D) TOPOLOGY: LINEAR (ii) MOLECULE TYPE: OTHER NUCLEIC ACID (iii) HYPOTHETICAL: NO (iv) ANTI-SENSE: NO (xi) SEQUENCE DESCRIPTION: SEQ ID NO: 8:

TTTGTGGGTG GGGGG                                                    15

(2) INFORMATION FOR SEQ ID NO: 9:

(i) SEQUENCE CHARACTERISTICS:
            (A) LENGTH: 15 BASE PAIRS
            (B) TYPE:  NUCLEIC ACID
            (C) STRANDEDNESS: SINGLE
            (D) TOPOLOGY: LINEAR (ii) MOLECULE TYPE: OTHER NUCLEIC ACID (iii) HYPOTHETICAL: NO (iv) ANTI-SENSE: NO (xi) SEQUENCE DESCRIPTION: SEQ ID NO: 9:

GGGTGGGGGG GTGGC                                                    15

(2) INFORMATION FOR SEQ ID NO: 10:

(i) SEQUENCE CHARACTERISTICS:
            (A) LENGTH: 15 BASE PAIRS
            (B) TYPE:  NUCLEIC ACID
            (C) STRANDEDNESS: SINGLE
            (D) TOPOLOGY: LINEAR (ii) MOLECULE TYPE: OTHER NUCLEIC ACID (iii) HYPOTHETICAL: NO (iv) ANTI-SENSE: NO (xi) SEQUENCE DESCRIPTION: SEQ ID NO: 10:

TGGGGGGAGC GAATA                                                    15

(2) INFORMATION FOR SEQ ID NO: 11:

(i) SEQUENCE CHARACTERISTICS:
            (A) LENGTH: 15 BASE PAIRS
            (B) TYPE:  NUCLEIC ACID
            (C) STRANDEDNESS: SINGLE
            (D) TOPOLOGY: LINEAR (ii) MOLECULE TYPE: OTHER NUCLEIC ACID (iii) HYPOTHETICAL: NO (iv) ANTI-SENSE: NO (xi) SEQUENCE DESCRIPTION: SEQ ID NO: 11:

TGAATCATGG GGGAC                                                   15

(2) INFORMATION FOR SEQ ID NO: 12:

(i) SEQUENCE CHARACTERISTICS:
        (A) LENGTH: 15 BASE PAIRS
        (B) TYPE: NUCLEIC ACID
        (C) STRANDEDNESS: SINGLE
        (D) TOPOLOGY: LINEAR (ii) MOLECULE TYPE: OTHER NUCLEIC ACID (iii) HYPOTHETICAL: NO (iv) ANTI-SENSE: NO (xi) SEQUENCE DESCRIPTION: SEQ ID NO: 12:

GAAAGGTTAA GCGAC                                                   15

(2) INFORMATION FOR SEQ ID NO: 13:

(i) SEQUENCE CHARACTERISTICS:
        (A) LENGTH: 15 BASE PAIRS
        (B) TYPE: NUCLEIC ACID
        (C) STRANDEDNESS: SINGLE
        (D) TOPOLOGY: LINEAR (ii) MOLECULE TYPE: OTHER NUCLEIC ACID (iii) HYPOTHETICAL: NO (iv) ANTI-SENSE: NO (xi) SEQUENCE DESCRIPTION: SEQ ID NO: 13:

ATTGGTTAAG GCGAC                                                   15

(2) INFORMATION FOR SEQ ID NO: 14:

(i) SEQUENCE CHARACTERISTICS:
        (A) LENGTH: 12 AMINO ACIDS
        (B) TYPE: AMINO ACID
        (C) STRANDEDNESS: SINGLE
        (D) TOPOLOGY: LINEAR (ii) MOLECULE TYPE: PEPTIDE (iii) HYPOTHETICAL: NO (iv) ANTI-SENSE: NO (xi) SEQUENCE DESCRIPTION: SEQ ID NO: 14:

Arg Val Leu Asp Arg Ala Ala Arg Gln Arg Arg Ile
                 5                  10

(2) INFORMATION FOR SEQ ID NO: 15:

(i) SEQUENCE CHARACTERISTICS:
        (A) LENGTH: 12 AMINO ACIDS
        (B) TYPE: AMINO ACID
        (C) STRANDEDNESS: SINGLE
        (D) TOPOLOGY: LINEAR (ii) MOLECULE TYPE: PEPTIDE (iii) HYPOTHETICAL: NO (iv) ANTI-SENSE: NO (xi) SEQUENCE DESCRIPTION: SEQ ID NO: 15:

Tyr Cys Thr Val Arg Cys Leu Gly Thr His Gln Glu
                  5                  10

(2) INFORMATION FOR SEQ ID NO: 16:

(i) SEQUENCE CHARACTERISTICS:
        (A) LENGTH: 697 BASE PAIRS
        (B) TYPE: NUCLEIC ACID
        (C) STRANDEDNESS: SINGLE
        (D) TOPOLOGY: LINEAR (ii) MOLECULE TYPE: OTHER NUCLEIC ACID (iii) HYPOTHETICAL: NO (iv) ANTI-SENSE: NO (xi) SEQUENCE DESCRIPTION: SEQ ID NO: 16:

```
CGGCNCGAGC TCGTGCCGCT TCGGTTCGCT CCCAGGACCC CGGGCAGCGG        50

CTGGTGCTGG ACCGGGCTGC CCGGCTGCGT CNCATCAACC GGCAGCTGGA       100

GGCCCTGGAG AATGACTACT TTCAGGATGA CTCCCATCGG GACTCCCTCN       150

NCTCGGCAAG AGACTGCCTC AGTTTGATTA CTATTCGGAC ACTGGAAAGA       200

AANAGAANAA NAATACCCGA GGTGATCATT TTAAACTTCG CTTCCGAAAA       250

AACTTTCAGG CCCTGTTGGA GGAGCAGAAC TTGAGTGTGG CCGAGGGCCT       300

AACTACCTGA CGGCCTGTGC GGGACCCCCA TCGCGGCCCC AGCGCCCCTT       350

CTGTGCTGTC TGTGGCTTCC CATCCCCCTA CACCTGTGTC AGCTGCGGTG       400

CCCGGTACTG CACTGTGCGC TGTCTGGGGA CCCACCAGGA GACCAGGTGT       450

CTGAAGTGGA CTGTGTGAGC CTGGGCATTC CAGAGAGGAA GGGCCGCTGT       500

CCACTGCCCG GCCTTCAGAA AGACAGAATT GCATCACCCA ATGCAGGGGG       550

AGCTTTTCCT GGACNNAGGG AGGNGCCGCT CNTTCACCAA ACAAAACTGT       600

GTCTCATCTG CCAGGAAAGA CCAGCTTCAC TCCTGGGAAC NGTCTGGCAG       650

GTAGGCTGGG CCCCCCAGTG CTGTTAGAAT AAAAAGCCTC GTGCCGG          697
```